(12) United States Patent
Chen et al.

(10) Patent No.: US 6,908,450 B1
(45) Date of Patent: Jun. 21, 2005

(54) SYRINGE PROTECTIVE STRUCTURE

(76) Inventors: Chang-Tzu Chen, 2F, No. 205, Sec. 5, Mingshen E. Road, Taipei (TW); Chin-Ping Ting, No. 20, Alley 17, Lane 4, Jiaan W. Road, Lungtan Shiang, Taoyuan Hsien (TW); Chung-Kuei Lin, No. 145-5, Shi-Nan Road, U-Ryh Hsiang, Taichung Hsien (TW)

( * ) Notice: Subject to any disclaimer, the term of this patent is extended or adjusted under 35 U.S.C. 154(b) by 0 days.

(21) Appl. No.: 10/831,003

(22) Filed: Apr. 23, 2004

(30) Foreign Application Priority Data

Feb. 27, 2004 (TW) .................................... 93202878 U

(51) Int. Cl.⁷ .............................................. A61M 5/18
(52) U.S. Cl. ..................................................... 604/110
(58) Field of Search ................................ 604/110, 187, 604/192, 197, 198, 263

(56) References Cited

U.S. PATENT DOCUMENTS

| | | | | |
|---|---|---|---|---|
| 4,973,308 A | * | 11/1990 | Borras et al. | 604/110 |
| 4,978,340 A | * | 12/1990 | Terrill et al. | 604/195 |
| 5,415,648 A | * | 5/1995 | Malay et al. | 604/181 |
| 6,077,245 A | * | 6/2000 | Heinrich et al. | 604/110 |
| 6,149,630 A | * | 11/2000 | Robinson | 604/198 |

* cited by examiner

*Primary Examiner*—Sharon Kennedy
(74) *Attorney, Agent, or Firm*—Law Offices of John Chupa & Associates, P.C.

(57) ABSTRACT

This invention discloses a syringe protective structure comprising a barrel which is a hollow cylinder having an opening disposed at a front end of the barrel, a barrel chamber therein, and a front blocking section and a rear blocking section inwardly protruded towards the opening proximate to a rear end of the barrel to define a blocking groove; and a relay base which is a hollow cylinder sheathed into the barrel chamber and has a base protrusion protruded from a front end of the relay base and an embedded hole disposed at the rear end of the relay base and interconnected with the base protrusion, and at least two resilient brackets being protruded from the periphery of the bottom of the base; by means of pushing the plunger of a liquid medication tube and the embedded hole forward, the liquid medication tube together with the push rod and the relay base move forward to the front of the barrel, such that the base protrudes out of the barrel opening and allows the needle to draw liquid medication into the barrel, and after the injection, the barrel is pushed forward to latch and fix the resilient brackets into the blocking groove.

9 Claims, 6 Drawing Sheets

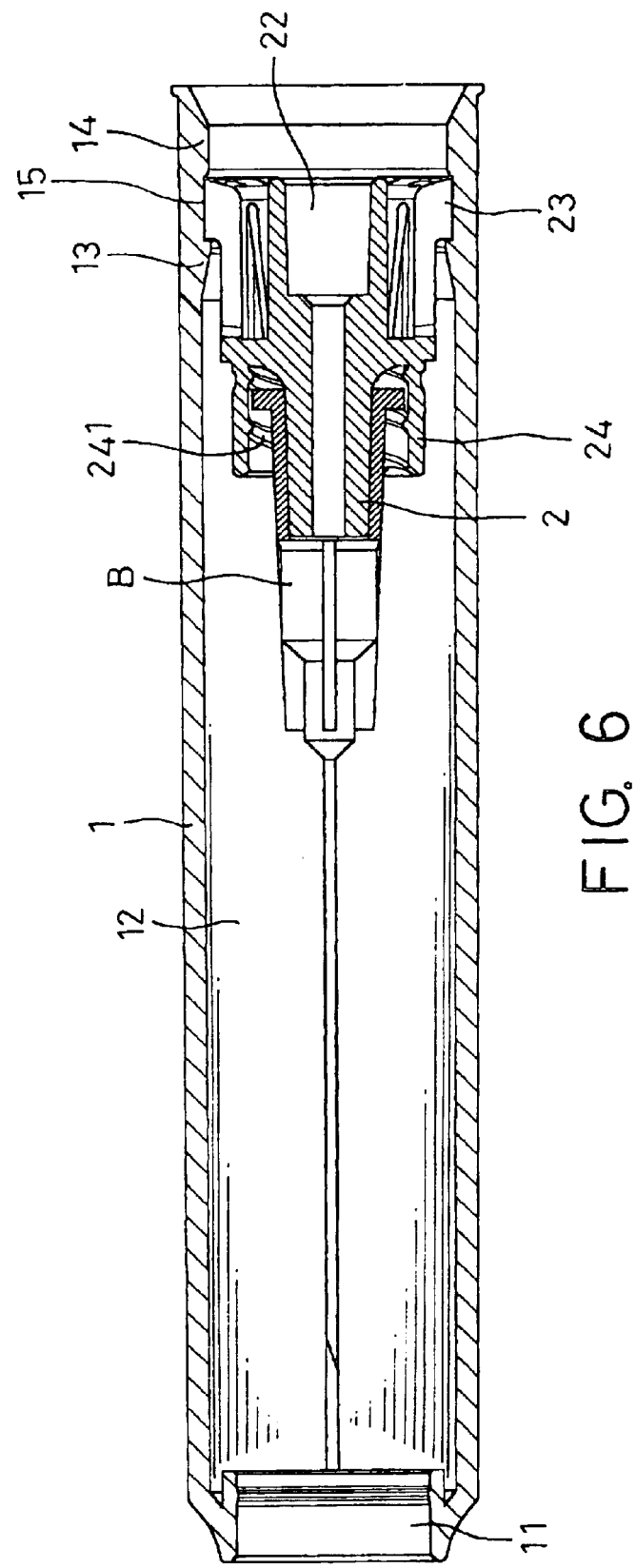

SYRINGE PROTECTIVE STRUCTURE

BACKGROUND OF THE INVENTION

1. Field of the Invention

The present invention relates to a syringe protective structure, more particularly to a syringe protective structure that prevents reusing the needle after an injection and protects medical staffs from being pierced by accident.

2. Description of the Related Art

Injections are very common in medical practices. In general, a liquid medication is drawn into a syringe and then injected into a human body. Therefore, a syringe is necessary for such medical treatment.

As the risk of medical treatment rises and individual safety and sanitation are taken into consideration, the disposal type or one-time-use type injection devices become a mainstream. Particularly in recent years, we often see infections such as AIDS or hepatitis caused by being pierced by a syringe. Therefore, medical staffs including doctors and nurses pay special attention to injections, and it is utmost importance to select the right syringe and prevent the reuse of syringes.

The conventional syringes generally comprise a liquid medication tube, a needle base connected to the front end of the liquid medication syringe, and a push rod slidably disposed inside the liquid medication tube. To keep the needle from being exposed to the outside, the syringe usually adds a needle cover to cover the needle. In order to prevent reusing the syringe after an injection, there are prior arts regarding the protection methods, and there are patented inventions for such protection.

The inventor of this invention had filed a Taiwan Utility Model Application No. 092221768 entitled "PROTECTIVE INJECTION NEEDLE" on Dec. 11, 2003 and disclosed a sleeve with a sleeve front on the front end, a chamber is formed inside said sleeve, a pair of blocking slots with a corresponding blocking piece face to face are on the inner center of said sleeve, a pair of none-penetrated fastening slots face to face are on the back of the inner wall of said sleeve, a pair of sleeve rings are on the front inner wall and back inner wall of said sleeve, a pair of none-penetrated stopping slots face to face are on the back inner wall of said sleeve, a sleeve path spans two said sleeve rings a needle base fastens a needle with a needle stand and connects to the barrel, a none-penetrated base slot corresponding to said blocking slot is on said needle base, a fastening tenon corresponding to said fastening slot is on a flat fastening plane, while assembly, said blocking piece is inserted into said blocking slot, said fastening tenon also falls into said fastening slot, said blocking piece is in said base slot, users connect the barrel and the needle stand for medicine, turn certain angle to have said fastening tenon fall into said sleeve path, push needle out from said sleeve front, pull the plunger outward to suck medicine, after injection, the barrel and the plunger are pulled backward, said fastening also goes backward along said sleeve path, falls into said stopping slot and stops. Thus, the invention can achieve the objectives of preventing the syringe from being reused or the people from being pierced by accident.

SUMMARY OF THE INVENTION

In view of the foregoing shortcomings, the inventors of the present invention based on years of experience on the related industry and the spirit of improving the product to prevent medical staffs from being pierced by the needle by accident and prevent patients from being injected by a reused syringe to conduct extensive researches and experiments, and finally invented the syringe protective structure in accordance with the invention.

The primary objective of the present invention is to provide a syringe protective structure comprising a barrel which is a hollow cylinder having an opening disposed at a front end of the barrel, a barrel chamber therein, and a front blocking section and a rear blocking section inwardly protruded towards the opening proximate to a rear end of the barrel to define a blocking groove; and a relay base which is a hollow cylinder sheathed into the barrel chamber and has a base protrusion protruded from a front end of the relay base and an embedded hole disposed at the rear end of the relay base and interconnected with the base protrusion, and at least two resilient brackets being protruded from the periphery of the bottom of the base; by means of pushing the plunger of a liquid medication tube and the embedded hole forward, the liquid medication tube together with the push rod and the relay base move forward to the front of the barrel, such that the base protrudes out of the barrel opening and allows the needle to draw liquid medication into the barrel, and the barrel is pushed forward to latch and fix the resilient brackets into the blocking groove after the injection is completed.

BRIEF DESCRIPTION OF THE DRAWINGS

To make it easier for our examiner to understand the objective of the invention, its structure, innovative features, and performance, we use a preferred embodiment together with the attached drawings for the detailed description of the invention, wherein:

FIG. 6 is a cross-sectional view of the liquid medication tube and the push rod being separated from the protective structure after the needle is withdrawn according to the present invention.

DETAILED DESCRIPTION OF THE PREFERRED EMBODIMENTS

Figure 1:
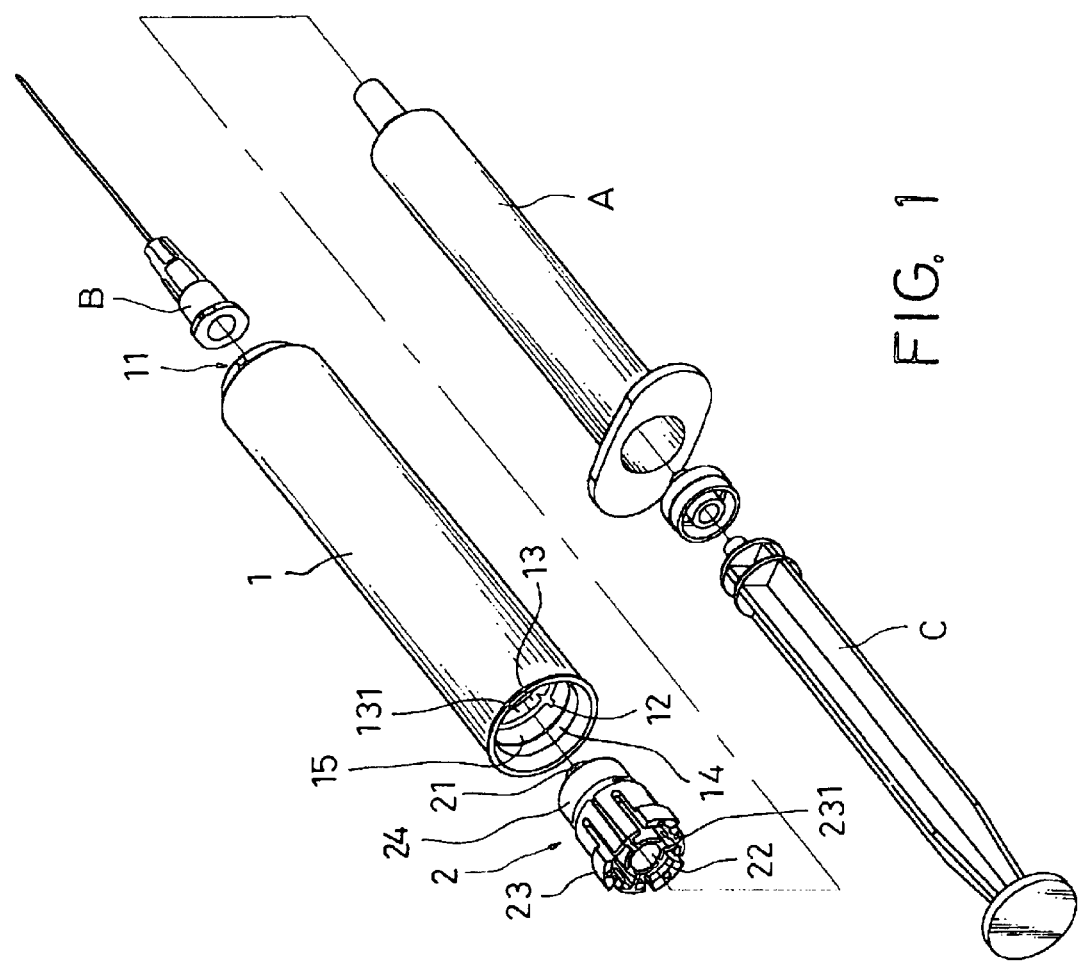
FIG. 1 is an exploded view of the syringe protective structure according to the present invention.
Figure 2:
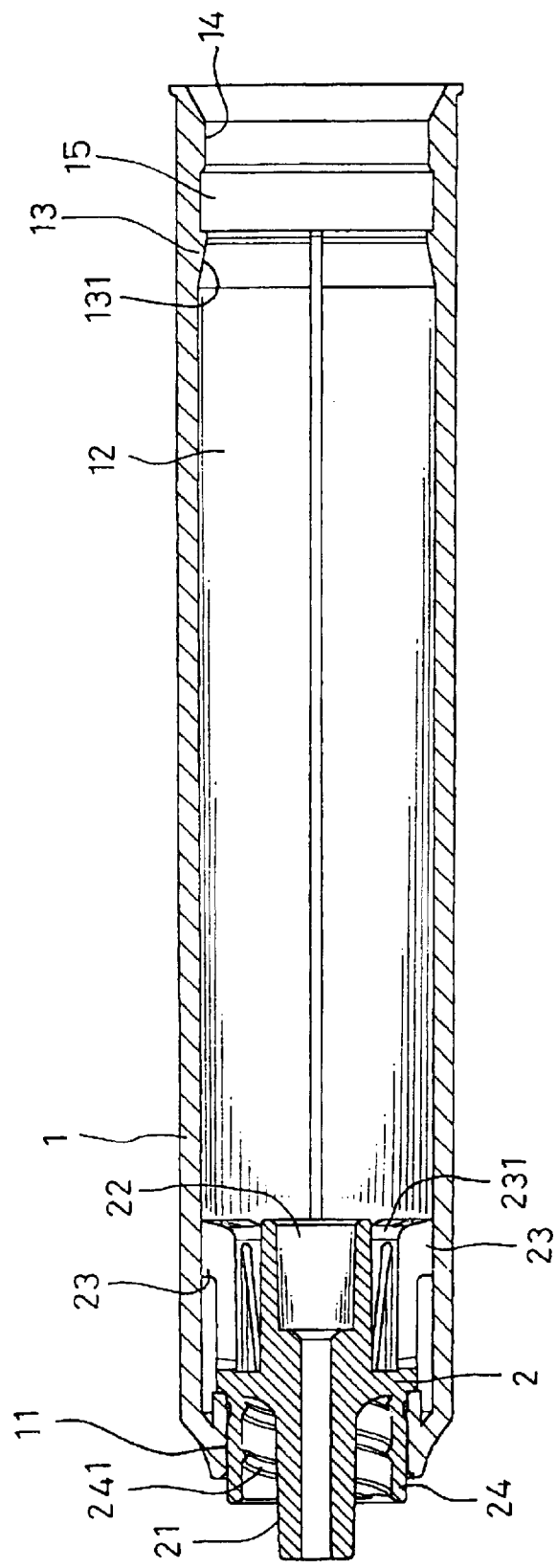
FIG. 2 is a cross-sectional view of the assembled structure of the syringe protective structure according to the present invention.

Please refer to FIGS. 1 and 2 for the syringe protective structure of the present invention, which comprises a barrel 1 and a relay base connected to a liquid medication tube A.

The barrel 1 is a cylindrical object having an opening 11 disposed at its front end for allowing a base protrusion 21 at the front end a relay base 2 to extend outward or withdraw inward, and a barrel chamber 12 disposed in the barrel 1. To empower the invention to have the protective mechanism, a pair of circular front blocking section 13 and rear blocking section 14 are disposed in the barrel chamber 12 and protruded inwardly at a position proximate to the opening to define a blocking groove 15. For the relay base 2 to be withdrawn and entered successfully into the blocking groove 15, an aslant surface 131 is formed on the relay base 2 to guide and latch the relay base 2 into the blocking groove 15. Further, to facilitate the injection molding, the height of the front blocking section 13 is slightly larger than the height of the rear blocking section 14.

The relay base 2 is a hollow cylinder, having a base protrusion 21 protruded from its front for connecting a needle base B. However it is not limited to such arrangement; a needle could be coupled to the base protrusion 21 directly, which still falls within the scope of the claims of the invention. An embedded hole 22 interconnected to the base protrusion 21 is disposed at the center of the rear side of the relay base 2, and the embedded hole 22 is coupled to the plunger at the front end of the liquid medication tube A. In addition, at least two resilient brackets 23 are extended laterally from the periphery of the bottom of the relay base 2. In the figure, three equiangular brackets 23 are shown, and each of the upper and lower sides has a channel 231 for providing the resilience required for the expansion and contraction of the brackets 23.

Please refer to FIG. 2. When the syringe protective structure of the invention is assembled, it only needs to use a tool to drive the brackets 23 into the relay base 2 to pass through the front and rear blocking sections 13, 14 easily and be fixed in front of the front blocking section 13.

Figure 3:
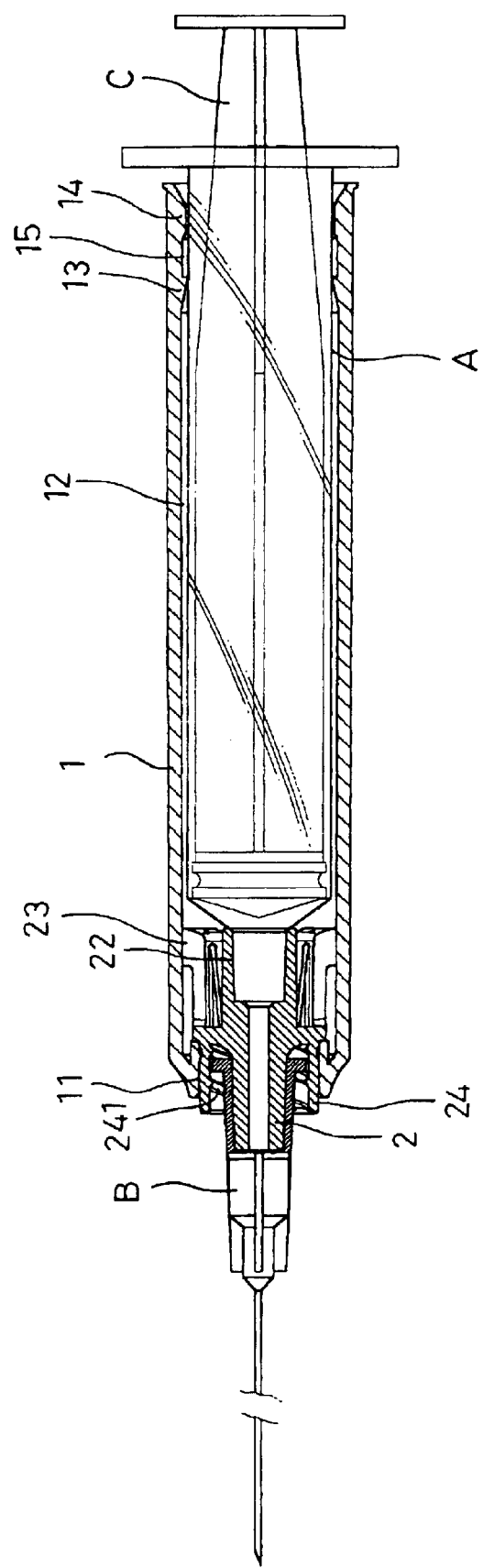
FIG. 3 is a cross-sectional view of the syringe protective structure being coupled with the needle according to the present invention.
Figure 4A:
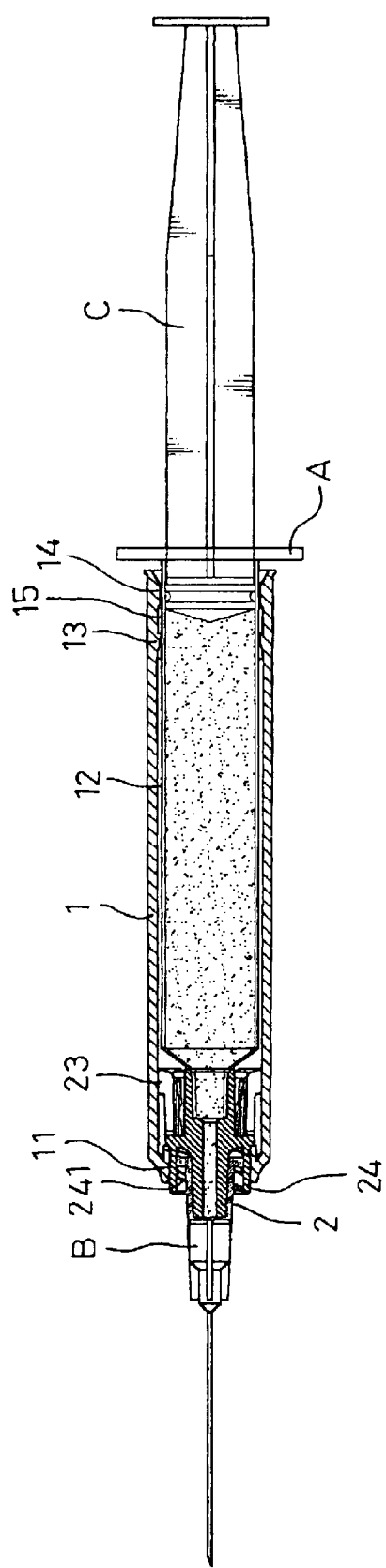
FIGS. 4a and 4b are cross-sectional views of the syringe protective structure drawing liquid medication into the barrel and after an injection is completed according to the present invention respectively.
Figure 4B:
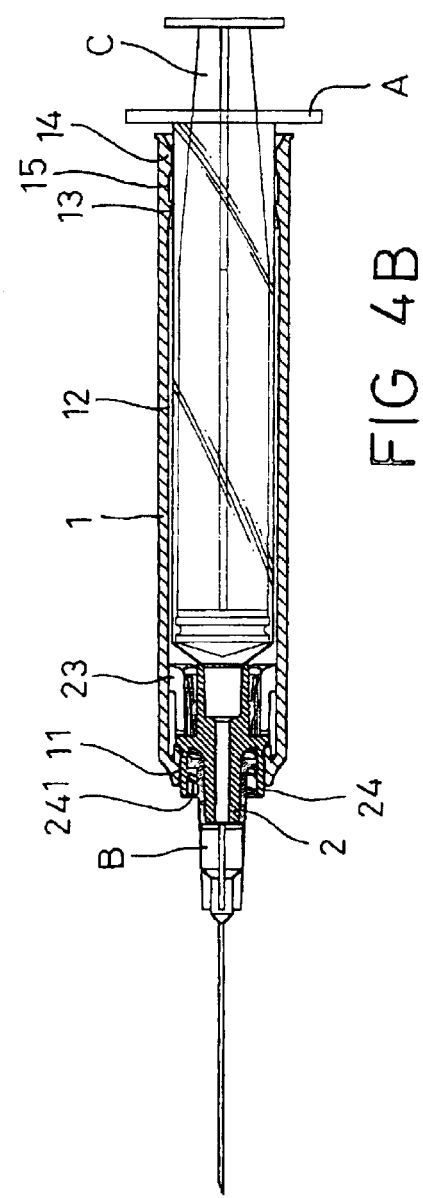

Please refer to FIG. 3 for the syringe protective structure of the invention being connected to a needle. The liquid medication tube A is passed into the opening at the bottom of the barrel 1, so that the front end of the syringe is engaged into the embedded hole 22 and pushes the liquid medication tube A, and synchronously pushes the brackets 23 of the relay base 2 along the wall of the barrel until the brackets 23 press the front of the barrel 1 and drive the base protrusion 21 to be extended from the barrel opening 11. Then, a medical staff can connect the needle base B with the base protrusion 21 in order to insert the needle into the liquid medication bottle and then pull the push rod C backward and allow the liquid medication to pass through the needle base B and the relay base 2 and be saved in the liquid medication tube A (as shown in FIG. 4a). Thus, the medical staff can perform the injection as shown in FIG. 4b.

Figure 5:
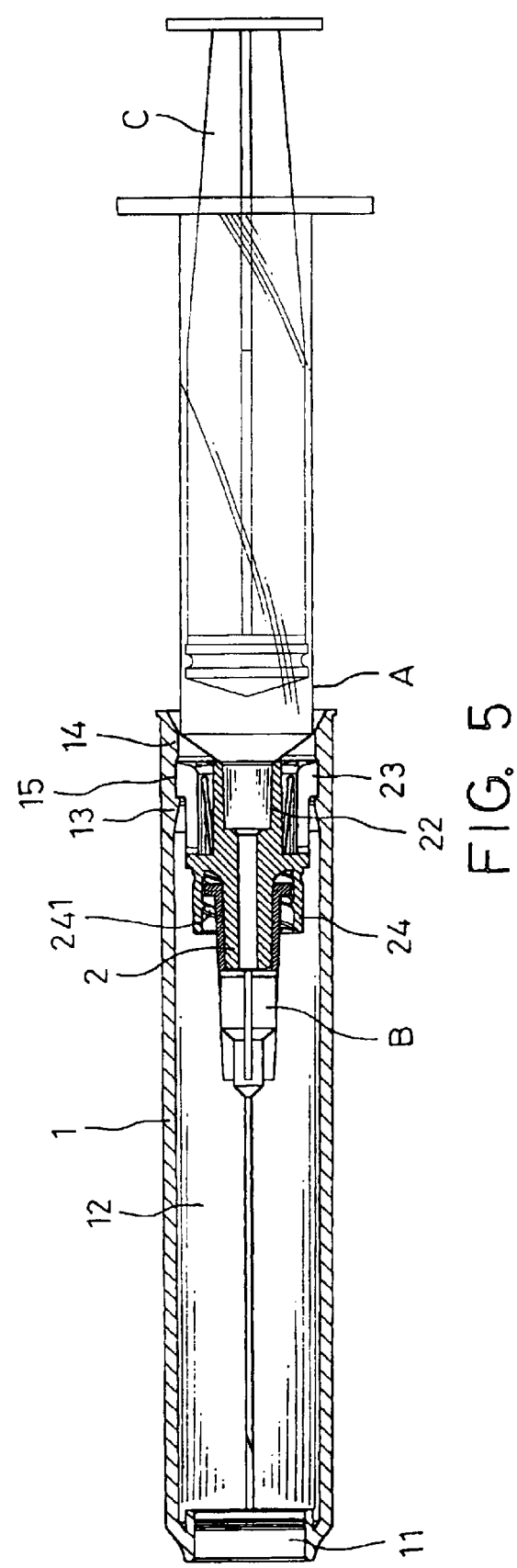
FIG. 5 is a cross-sectional view of the syringe protective structure with the syringe being withdrawn according to the present invention.

After the injection is completed, the liquid medication tube A together with the push rod C, the relay base 2 and the needle base B are pulled backward, so that the brackets 23 moves along the inner wall of the barrel 1 and falls into the blocking groove 15 when the bracket 23 passes through the aslant surface 131 of the front blocking section 13, and finally stops at the rear blocking section 14, and thus constituting a latch state as shown in FIG. 5. Therefore, the relay base 2 and the needle base B will not fall out from the barrel 1, and the liquid medication tube A and the push rod C can be separated from the barrel 1 (as shown in FIG. 6) for recycles. The invention provides a protective measure for prohibiting the reuse of the barrel 1 including the relay base 2 of the needle.

Further, a section of latch ring 24 is extended horizontally from the external periphery of the end section of the base protrusion 21 in order to enhance the connection between the base protrusion 21 and the needle base B, and a thread 241 disposed inside the latch ring 24 is used for connecting the needle base B.

In summation of the description above, the present invention not only greatly reduces the complexity of the components and simplifies the structure, but also greatly lowers the manufacturing cost. Furthermore, the relay base and the barrel are fixed and will not fall out, which can assure the safety during the transportation and storage processes. Further, the base protrusion of the relay base can have a needle directly or go with various needle bases for a more flexible application. The latch can pull the relay base back after an injection is completed. Unless being damaged by external forces, the relay base together with the needle base can be fixed into the barrel. Such arrangement can keep the needle from being exposed and achieve the safety purpose. The invention upgrades the conventional syringe to a safety syringe, which is definitely a great idea for the object of same sort.

While the invention has been described by way of examples and in terms of preferred embodiments, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

In summation of the above description, the present invention herein enhances the performance than the conventional structure and further complies with the patent application requirements and is submitted to the Patent and Trademark Office for review and granting of the commensurate patent rights.

What is claimed is:

1. A syringe protective structure, comprising:
    a barrel, being a hollow cylinder and having an opening disposed at its front end, a barrel chamber therein, and a front blocking section and a rear blocking section inwardly protruded towards said opening proximate to a rear end of said barrel to define a blocking groove; and
    a relay base, being a hollow cylinder sheathed into said barrel chamber and having a base protrusion protruded from a front end of said relay base and an embedded hole disposed at the rear end of said relay base and interconnected with said base protrusion, and at least two resilient brackets being protruded from the periphery of the bottom of said base; a plunger; and a liquid medication tube;
    by means of pushing said plunger of said liquid medication tube and said embedded hole forward, said liquid medication tube together with a push rod and said relay base moves forward to the front of said barrel, such that the base protrudes out of the barrel opening and allows the needle to draw a liquid medication into said barrel, and said barrel is pushed forward to latch and fix said resilient brackets into said blocking groove after the injection.

2. The syringe protective structure of claim 1, wherein said front blocking section had an aslant surface at its front end.

3. The syringe protective structure of claim 1, wherein said front and rear blocking sections are in a circular shape.

4. The syringe protective structure of claim 1 comprising three resilient brackets.

5. The syringe protective structure of claim 1, wherein said bracket has a transversal channel disposed individually at the upper and lower edges of said brackets.

6. The syringe protective structure of claim 1, wherein said base protrusion has a needle.

7. The syringe protective structure of claim 1, wherein said base protrusion is coupled with a needle base having a needle.

8. The syringe protective structure of claim 7, wherein said base protrusion comprises a section of a latch ring extended horizontally at the external periphery of the end section of said base protrusion and a threat disposed inside said latch ring for connecting said needle base.

9. The syringe protective structure of claim 1, wherein said front blocking section has a larger than that of said rear blocking section.

* * * * *